United States Patent [19]

Liston

[11] 4,455,243
[45] Jun. 19, 1984

[54] SUCCINIMIDE COMPLEXES OF BORATED FATTY ACID ESTERS OF GLYCEROL AND LUBRICATING OIL COMPOSITIONS CONTAINING SAME

[75] Inventor: Thomas V. Liston, San Rafael, Calif.

[73] Assignee: Chevron Research Company, San Francisco, Calif.

[21] Appl. No.: 469,500

[22] Filed: Feb. 24, 1983

[51] Int. Cl.$^3$ .................... C10M 1/26; C10M 1/32
[52] U.S. Cl. ................... 252/49.6; 252/32.7 E; 252/51.5 A; 252/33.3; 252/49.7; 252/49.8; 260/462 R; 548/405
[58] Field of Search ............ 252/32.7 E, 49.6, 51.5 A, 252/33.3; 548/405; 260/462 R

[56] References Cited

U.S. PATENT DOCUMENTS

3,254,025  5/1966  Le Suer ........................ 252/49.6
4,295,983 10/1981  Papay et al. ................ 252/49.6
4,370,248  1/1983  Horodysky et al. ........ 252/49.6

*Primary Examiner*—Jacqueline V. Howard
*Attorney, Agent, or Firm*—D. A. Newell; J. M. Whitney; G. F. Swiss

[57] ABSTRACT

Lubricating oils containing borated fatty acid esters of glycerol-succinimide complex have been found to reduce fuel consumption in an internal combustion engine.

16 Claims, No Drawings

SUCCINIMIDE COMPLEXES OF BORATED FATTY ACID ESTERS OF GLYCEROL AND LUBRICATING OIL COMPOSITIONS CONTAINING SAME

BACKGROUND OF THE INVENTION

1. Field of the Invention

The invention is concerned with the product obtained by reacting borated fatty acid esters of glycerol with a succinimide and the use of said product in lubricant compositions.

2. Description of the Prior Art

With the crisis associated with diminishing amounts of fossil fuel and the rapidly increasing prices for this fuel, there has been a great deal of interest in reducing the amount of fuel consumed by automobile engines, and the like.

Thus, there is a great need to find lubricants that reduce the overall friction in the engine, thus reducing the energy requirements thereto.

U.S. Pat. No. 4,201,684 teaches lubricating oils containing sulfurized fatty acid amides, esters or esteramides of alkoxylated amines, which reduce friction between sliding metal surfaces in internal combustion engines.

U.S. Pat. No. 4,167,486 teaches lubricating oils containing certain acid esters having double bonds or the dimer or trimer of such acid esters. Reductions in fuel consumption in an internal combustion engine are claimed by using the lubricating oils in the crankcase of the engine.

U.S. Pat. No. 3,151,077 teaches the use of borated monoacylated trimethylol alkanes as motor fuel and lubricating oil additives. The additives are taught to reduce the incidence of surface ignition in an internal combustion engine and to inhibit the build-up of carburetor deposits.

U.S. Pat. No. 2,795,548 discloses the use of lubricating oils compositions containing borated glycerol monooleate. The oil compositions are used in the crankcase of an internal combustion engine in order to reduce oxidation of the oil and corrosion of the metal parts of the engine.

There is a problem with the use of borated fatty acid esters of glycerol in lubricating oils since they are sensitive to moisture and hydrolyze readily. The hydrolysis leads to haze and/or precipitate formation which must be filtered out prior to use. Also, glycerol oleate which is generated as a result of the hydrolysis causes bearing corrosion problems and/or precipitate problems in the presence of certain zinc dihydrocarbyl dithiophosphonates and metal phenates.

It has now been found that the borated fatty acid esters of glycerol may be stabilized against hydrolysis by complexing the borated fatty acid esters of glycerol with an alkenyl or alkyl mono or bis succinimide.

Most importantly, it has now been found that lubricating the crankcase of an internal combustion engine with a lubricating oil containing the reaction product of a borated fatty acid ester of glycerol and a succinimide reduces the fuel consumption of the engine.

SUMMARY OF THE INVENTION

According to the present invention, lubricating oils are provided which reduce friction between sliding metal surfaces and which are especially useful in the crankcase of internal combustion engines. The reduced friction results from the addition to the lubricating oil of small amounts of a complex prepared by reacting a borated fatty acid ester of glycerol and an alkyl or alkenyl mono or bis succinimide.

Thus this invention relates to a lubricating oil composition comprising an oil of lubricating viscosity and an effective amount to reduce friction of a complex prepared by reacting (a) a borated fatty acid ester of glycerol or mixtures thereof and (b) an oil soluble alkyl or alkenyl mono- or bis-succinimide.

Other additives may also be present in the lubricating oil in order to obtain a proper balance of properties such as dispersancy, corrosion, wear and oxidation inhibition which are critical for the proper operation of an internal combustion engine.

Further, in accordance with the invention, there is provided a method for reducing fuel consumption of an internal combustion engine by treating the moving surfaces thereof with the lubricating oil composition described above. Specifically, improvements in fuel mileage of from 2 to 3% on the average have been observed in engine tests. This fuel economy improvement can be obtained in both compression-ignition engines, that is, diesel engines, and spark-ignition engines, that is, gasoline engines.

DETAILED DESCRIPTION OF THE INVENTION

The borated fatty acid esters of glycerol are prepared by borating a fatty acid ester of glycerol with boric acid with removal of the water of reaction. Preferably, there is sufficient boron present such that each boron will react with from 1.5 to 2.5 hydroxyl groups present in the reaction mixture.

The reaction may be carried out at a temperature in the range of 60° C. to 135° C., in the absence or presence of any suitable organic solvent such as methanol, benzene, xylenes, toluene, neutral oil and the like.

Fatty acid esters of glycerol can be prepared by a variety of methods well known in the art. Many of these esters, such as glycerol monooleate and glycerol tallowate, are manufactured on a commercial scale. The esters useful for this invention are oil-soluble and are preferably prepared from $C_8$ to $C_{22}$ fatty acids or mixtures thereof such as are found in natural products. The fatty acid may be saturated or unsaturated. Certain compounds found in acids from natural sources may include licanic acid which contains one keto group. Most preferred $C_8$ to $C_{22}$ fatty acids are those of the formula R—COOH wherein R is alkyl or alkenyl.

The fatty acid monoester of glycerol is preferred, however, mixtures of mono- and diesters may be used. Preferably any mixture of mono- and diester contains at least 40% of the monoester. Most preferably, mixtures of mono- and diesters of glycerol contain from 40 to 60 percent by weight of the monoester. For example, commerical glycerol monooleate contains a mixture of from 45% to 55% by weight monoester and from 55% to 45% diester.

Preferred fatty acids are oleic, stearic, isostearic, palmitic, myristic, palmitoleic, linoleic, lauric, linolenic, and eleostearic, and the acids from the natural products tallow, palm oil, olive oil, peanut oil, corn oil, neat's foot oil and the like.

A particularly preferred acid is oleic acid.

The borated fatty acid esters are stabilized against hydrolysis by reacting the esters with an alkyl or alkenyl mono- or bis-succinimide.

The oil soluble alkenyl or alkyl mono- or bis-succinimides which are employed in this invention are generally known as lubricating oil detergents and are described in U.S. Pat. Nos. 2,992,708, 3,018,291, 3,024,237, 3,100,673, 3,219,666, 3,172,892 and 3,272,746, the disclosures of which are incorporated by reference. The alkenyl succinimides are the reaction product of a polyolefin polymer-substituted succinic anhydride with an amine, preferably a polyalkylene polyamine. The polyolefin polymer-substituted succinic anhydrides are obtained by reaction of a polyolefin polymer or a derivative thereof with maleic anhydride. The succinic anhydride thus obtained is reacted with the amine compound. The preparation of the alkenyl succinimides has been described many times in the art. See, for example, U.S. Pat. Nos. 3,390,082, 3,219,666 and 3,172,892, the disclosure of which are incorporated herein by reference. Reduction of the alkenyl substituted succinic anhydride yields the corresponding alkyl derivative. A product comprising predominantly mono- or bis-succinimide can be prepared by controlling the molar ratios of the reactants. Thus, for example, if one mole of amine is reacted with one mole of the alkenyl or alkyl substituted succinic anhydride, a predominantly monosuccinimide product will be prepared. If two moles of the succinic anhydride are reacted per mole of polyamine, a bis-succinimide will be prepared.

Particularly good results are obtained with the lubricating oil compositions of this invention when the alkenyl succinimide is a polyisobutene-substituted succinic anhydride of a polyalkylene polyamine.

The polyisobutene from which the polyisobutene-substituted succinic anhydride is obtained by polymerizing isobutene and can vary widely in its compositions. The average number of carbon atoms can range from 30 or less to 250 or more, with a resulting number average molecular weight of about 400 or less to 3,000 or more. Preferably, the average number of carbon atoms per polyisobutene molecule will range from about 50 to about 100 with the polyisobutenes having a number average molecular weight of about 600 to about 1,500. More preferably, the average number of carbon atoms per polyisobutene molecule ranges from about 60 to about 90, and the number average molecular weight ranges from about 800 to 1,300. The polyisobutene is reacted with maleic anhydride according to well-known procedures to yield the polyisobutene-substituted succinic anhydride.

In preparing the alkenyl succinimide, the substituted succinic anhydride is reacted with a polyalkylene polyamine to yield the corresponding succinimide. Each alkylene radical of the polyalkylene polyamine usually has up to about 8 carbon atoms. The number of alkylene radicals can range up to about 8. The alkylene radical is exemplified by ethylene, propylene, butylene, trimethylene, tetramethylene, pentamethylene, hexamethylene, octamethylene, etc. The number of amino groups generally, but not necessarily, is one greater than the number of alkylene radicals present in the amine, i.e., if a polyalkylene polyamine contains 3 alkylene radicals, it will usually contain 4 amino radicals. The number of amino radicals can range up to about 9. Preferably, the alkylene radical contains from about 2 to about 4 carbon atoms and all amine groups are primary or secondary. In this case, the number of amine groups exceeds the number of alkylene groups by 1. Preferably the polyalkylene polyamine contains from 3 to 5 amine groups. Specific examples of the polyalkylene polyamines include ethylenediamine, diethylenetriamine, triethylenetetramine, propylenediamine, tripropylenetetramine, tetraethylenepentamine, trimethylenediamine, pentaethylenehexamine, di-(trimethylene)triamine, tri(hexamethylene)tetramine, etc.

Other amines suitable for preparing the alkenyl succinimide useful in this invention include the cyclic amines such as piperazine, morpholine and dipiperazines.

Preferably the alkenyl succinimides used in the compositions of this invention have the following formula:

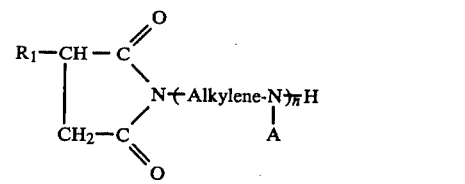

wherein:

a. $R_1$ represents an alkenyl group, preferably a substantially saturated hydrocarbon prepared by polymerizing aliphatic monoolefins. Preferably $R_1$ is prepared from isobutene and has an average number of carbon atoms and a number average molecular weight as described above;

b. the "Alkylene" radical represents a substantially hydrocarbyl group containing up to about 8 carbon atoms and preferably containing from about 2–4 carbon atoms as described hereinabove;

c. A represents a hydrocarbyl group, an amine-substituted hydrocarbyl group, or hydrogen. The hydrocarbyl group and the amine-substituted hydrocarbyl groups are generally the alkyl and amino-substituted alkyl analogs of the alkylene radicals described above. Preferably A represents hydrogen;

d. n represents an integer of from about 1 to 10, and preferably from about 3–5.

The alkenyl succinimide is present in the lubricating oil compositions of the invention in an amount effective to stabilize the borated fatty acid esters against hydrolysis and to act as a dispersant and prevent the deposit of contaminants formed in the oil during operation of the engine.

The complex, the exact structure of which is not known, may be formed by reacting the borated fatty acid esters of glycerol and the succinimide together neat at a temperature above the melting point of the mixture of reactants and below the decomposition temperature, or in a diluent in which both reactants are soluble. For example, the reactants may be combined in the proper ratio in the absence of a solvent to form a homogeneous product which may be added to the oil or the reactants may be combined in the proper ratio in a solvent such as toluene or chloroform, the solvent stripped off, and the complex thus formed may be added to the oil. Alternatively, the complex may be prepared in a lubricating oil as a concentrate containing from about 10 to 90% by weight of the complex, which concentrate may be added in appropriate amounts to the lubricating oil in which it is to be used or the complex may be prepared directly in the lubricating oil in which it is to be used.

The diluent is preferably inert to the reactants and products formed and is used in an amount sufficient to insure solubility of the reactants and to enable the mixture to be efficiently stirred.

Temperatures for preparing the complex may be in the range of from 25° C. to 200° C. and preferably 25° C. to 100° C. depending on whether the complex is prepared neat or in a diluent, i.e., lower temperatures may be used when a solvent is used.

Weight percent ratio of succinimide to borated fatty acid ester of glycerol to form the complex is in the range of 0.5:1 to 3:1 and preferably from 1:1 to 2:1 and most preferably 1:1. This latter ratio is preferred if the complex is made and/or stored neat or in the absence of solvent or lubricating oil and under atmospheric conditions.

The amount of additive required to be effective for reducing friction in lubricating oil compositions may range from 0.3% to about 10% by weight of the total lubricant composition and preferably is present in the range of from 1% to 5% by weight. The succinimide is present in the complex of the invention in an amount effective to stabilize the borated esters against hydrolysis and which allows the borated esters to function as effective friction reducing agents.

Also, the succinimide in the complex acts as a dispersant and prevents the deposition of contaminants formed in the oil during operation of the engine.

In General, the complexes of this invention may also be used in combination with other additive systems in conventional amounts for their known purpose.

For example, for application in modern crankcase lubricants, the base composition described above will be formulated with supplementary additives to provide the necessary stability, detergency, dispersancy, anti-wear and anti-corrosion properties.

Thus, as another embodiment of this invention, the lubricating oils to which the complexes prepared by reacting the borated fatty acid esters of glycerol and succinimides may contain an alkali or alkaline earth metal hydrocarbyl sulfonate, an alkali or alkaline earth metal phenate, and Group II metal salt dihydrocarbyl dithiophosphate.

Also, since the succinimides act as excellent dispersants, additional succinimide may be added to the lubricating oil compositions, above the amounts added in the form of the complex with the borated fatty acid esters of glycerol. The amount of succinimides can range up to about 20% by weight of the total lubricating oil compositions.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well known in the art. The hydrocarbyl group must have a sufficient number of carbon atoms to render the sulfonate molecule oil soluble. Preferably, the hydrocarbyl portion has at least 20 carbon atoms and may be aromatic or aliphatic, but is usually alkylaromatic. Most preferred for use are calcium, magnesium or barium sulfonates which are aromatic in character.

Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

The sulfonates may be neutral or overbased having base numbers up to about 400 or more. Carbon dioxide and calcium hydroxide or oxide are the most commonly used material to produce the basic or overbased sulfonates. Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols. One of the functions of the phenates is to act as a detergent and dispersant. Among other things, it prevents the deposit of contaminants formed during high temperature operation of the engine. The phenols may be mono- or polyalkylated.

The alkyl portion of the alkyl phenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material. Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, tricontyl, and the like. Other suitable synthetic sources of the alkyl radical include olefin polymers such as polypropylene, polybutylene, polyisobutylene and the like.

The alkyl group can be straight-chained or branch-chained, saturated or unsaturated (if unsaturated, preferably containing not more than 2 and generally not more than 1 site of olefinic unsaturation). The alkyl radicals will generally contain from 4 to 30 carbon atoms. Generally when the phenol is monoalkyl-substituted, the alkyl radical should contain at least 8 carbon atoms. The phenate may be sulfurized if desired. It may be either neutral or overbased and if overbased will have a base number of up to 200 to 300 or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2 to 13% by weight of the total composition. Most preferably, the overbased phenates are present from 0.2% to 5% by weight of the total composition. Preferred metals are calcium, magnesium, strontium or barium.

The sulfurized alkaline earth metal alkyl phenates are preferred. These salts are obtained by a variety of processes such as treating the neutralization product of an alkaline earth metal base and an alkylphenol with sulfur. Conveniently the sulfur, in elemental form, is added to the neutralization product and reacted at elevated temperatures to produce the sulfurized alkaline earth metal alkyl phenate.

If more alkaline earth metal base were added during the neutralization reaction than was necessary to neutralize the phenol, a basic sulfurized alkaline earth metal alkyl phenate is obtained. See, for example, the process of Walker et al, U.S. Pat. No. 2,680,096. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol.

Carbon dioxide and calcium hydroxide or oxide are the most commonly used material to produce the basic or "overbased" phenates. A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, columns 6 and 7, wherein these compounds and their preparation are described generally. Suitably, the Group II metal salts of the dihydrocarbyl dithiophosphoric acids useful in the lubricating oil composition of this invention contain from about 4 to about 12 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec.-butyl, hexyl, isohexyl, octyl, 2-ethylhexyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

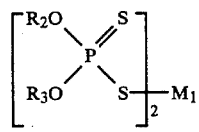

wherein:

e. $R_2$ and $R_3$ each independently represent hydrocarbyl radicals as described above, and f. $M_1$ represents a Group II metal cation as described above.

The dithiophosphoric salt is present in the lubricating oil compositions of this invention in an amount effective to inhibit wear and oxidation of the lubricating oil. The amount ranges from about 0.1 to about 4 percent by weight of the total composition, preferably the salt is present in an amount ranging from about 0.2 to about 2.5 percent by weight of the total lubricating oil composition. The final lubricating oil composition will ordinarily contain 0.025 to 0.25% by weight phosphorus and preferably 0.05 to 0.15% by weight.

The finished lubricating oil may be single or multigrade. Multigrade lubricating oils are prepared by adding viscosity index (VI) improvers. Typical viscosity index improvers are polyalkyl methacrylates, ethylene propylene copolymers, styrene diene copolymers and the like. So-called decorated VI improvers having both viscosity index and dispersant properties are also suitable for use in the formulations of this invention.

The lubricating oil used in the compositions of this invention may be mineral oil or in synthetic oils of lubricating viscosity and preferably suitable for use in the crankcase of an internal combustion engine. Crankcase lubricating oils ordinarily have a viscosity of about 1300 cst 0° F. to 22.7 cst at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_{6-12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. They usually include from about 90 to 10 weight percent of an oil of lubricating viscosity and from about 10 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

The following examples are offered to specifically illustrate the invention. These examples and illustrations are not to be construed in any way as limiting the scope of the invention.

EXAMPLE 1

Preparation of Borated Glycerol Monooleate

To a mixture containing 125.23 grams of glycerol monooleate (45% to 55% by weight) and glycerol dioleate (55% to 45% by weight) were added 30.92 grams boric acid and 250 mls. of xylene. The reaction mixture was heated at 99° to 141° C. for about nine and one-half hours under nitrogen at azeotropic conditions. 17.6 mls. of water were collected by a Dean Stark trap. The reaction product was filtered and stripped on a roto evaporator under vacuum to 135° C. to yield 128.35 grams. Analysis: boron 2.42% and 2.52% hydroxyl number 32 mg KOH/gm. Infrared spectroscopy analysis of the product shows no free glycerol-type hydroxyl stretching but does have strong BO—H bond and virtually no B—O—B-type absorption.

EXAMPLE 2

Oil blends were prepared as indicated in Table I using CC 100N oil and containing 1% by weight of the borated glycerol oleate prepared according to Example 1, with and without 0.66% by weight polyisobutenyl succinimide (prepared by reacting polyisobutenyl succinic anhydride wherein the number average molecular weight of the polyisobutenyl was about 950 and tetraethylenepentamine in a mole ratio of amine to anhydride of 0.87).

One hundred and fifty ml of each of the base oil and blends in a 250 ml beaker were placed in a humidity cabinet maintained at 100° F. and 90% relative humidity. The samples were rated for haze and sediment as a function of time.

TABLE I

| Formulation | Time - Days | Observation |
|---|---|---|
| Base oil | 1-3 | bright and clear |
| Base oil + 1% by weight Borated glycerol oleate | 1 | cloudy and precipitate formed |
| Base oil + 1% by weight | 1 | bright and clear |
| Borated glycerol oleate + 0.66% by weight polyisobutenyl succinimide | 3 | slight haze |

EXAMPLE 3

One part by weight of the borated glycerol oleate prepared according to Example 1 and 2 parts by weight of a 44%-by weight of polyisobutenyl succinimide (prepared by reacting polyisobutenyl succinic anhydride wherein the number average molecular weight of the polyisobutenyl was about 950 and tetraethylenepentamine in a mole ratio of amine to anhydride of 0.87) solution in oil (CC 100N) were heated together with mixing on a hot plate at 170° C. for 0.5 hours.

One hundred and fifty ml of the reaction mixture was placed in a 250 ml beaker and placed in a humidity cabinet maintained at 100° F. and 90% relative humidity. A 250 ml beaker containing 150 ml of only the borated glycerol oleate and no succinimide was also placed in the humidity cabinet for a comparison.

The borated glycerol oleate hydrolyzed and formed a skin of boric acid on its surface after about one minute in the humidity cabinet. The borated glycerol oleate-succinimide complexed material remained bright and clear after one week in the humidity cabinet. Even after three weeks, only a trace of haze appeared in the sample containing the complex.

EXAMPLE 4

Tests were carried out which demonstrate the improvements in fuel economy obtained by adding lubricating oil compositions of this invention to the crankcase of an automobile engine.

In this test, a 350 CID Oldsmobile engine was run on a dynamometer. An engine oiling system was devised in order to provide proper lubrication to the engine and also to provide the capability to change the oil without stopping the engine. Basically a dry sump system was used with an external pump providing lubrication to the engine. This pump was connected through valves to four external sumps. The positioning of the valves determined the oil used.

This test was repeated several times under constant conditions with base oil and then with the same oil containing 1.25, 1.50 and 2% by weight of the borated glycerol oleate-succinimide complexes prepared according to Example 3. The percent improvements in fuel economy using the compositions of the invention as compared to the base oil is shown in Table II.

TABLE II

| Fuel Economy Over Baseline Concentrations of Sample | |
|---|---|
| Concentration (% by weight) | % Improvement |
| 1.25 | 1.35 |
| 1.5 | 2.22 |
| 2.0 | 2.62 |

The comparisons in the test described above were made with Exxon 150N blended oil additionally containing 30 mmols/kg overbased magnesium hydrocarbyl sulfonate, 2.5% of a 44% by weight polyisobutenyl succinimide in oil (CC 100N), 20 mmoles/kg of overbased sulfurized calcium polypropylene phenate, 16 mmols/kg zinc di(alkyl)dithiophosphate, 5.5% of an aminated polyethylene/propylene/diene-based VI improver and 3 mmoles/kg of a sulfurized molybdenum succinimide complex.

Also, formulated crankcase oils each containing 2% by weight of a succinimide complex of borated glycerol mono-tallowate, borated glycerol monostearate and borated glycerol monolaurate in place of the borated glycerol oleate-succinimide complex in the above formulations are also effective in reducing fuel consumption in an internal combustion engine.

Tests have also indicated that the borated fatty acid ester of glycerol-succinimide complexes of this invention have no adverse effects on valve train wear such as cam and lifter wear as determined by the Standardized Sequence IIID Test, cam lobe wear as determined by the Standardized Sequence VD Test method Phase 9-L (according to candidate test for ASTM) and they are not corrosive to copper-lead bearings.

What is claimed is:

1. A composition comprising a complex prepared by reacting a borated fatty acid ester of glycerol or mixtures thereof and an oil soluble alkyl or alkenyl succinimide at 25° C. to 200° C. wherein the wt% ratio of succinimide to borated fatty acid ester of glycerol to form the complex is in the range of 0.5:1 to 3:1.

2. The composition according to claim 1 wherein said borated fatty acid ester of glycerol is a borated glycerol oleate or mixtures thereof and said succinimide is a polyisobutenyl succinimide of a polyalkylene polyamine.

3. The composition according to claim 2 wherein said succinimide is a polyisobutenyl succinimide of triethylenetetramine or polyisobutenyl succinimide of tetraethylenepentamine.

4. The composition according to claim 2 wherein said borated fatty acid ester of glycerol is a mixture containing from 45% to 55% by weight of borated glycerol monooleate and 55% to 45% by weight of borated glycerol dioleate.

5. The composition according to claim 2 wherein the borated fatty acid ester of glycerol is borated glycerol monooleate.

6. A lubricating oil composition comprising a major amount of an oil of lubricating viscosity and an effective amount to reduce friction of a complex prepared by reacting:
   (a) a borated fatty acid ester of glycerol or mixtures thereof; and
   an oil soluble alkyl or alkenyl succinimide at 25° C. to 200° C. wherein the wt% ratio of succinimide to borated fatty acid ester of glycerol to form the complex is in the range of 0.5:1 to 3:1.

7. The lubricating oil composition according to claim 6 wherein said borated fatty acid ester of glycerol is a borated glycerol oleate or mixtures thereof and said succinimide is a polyisobutenyl succinimide of a polyalkylene polyamine.

8. The lubricating oil composition according to claim 7 wherein said succinimide is a polyisobutenyl succinimide of triethylenetetramine or polyisobutenyl succinimide of tetraethylenepentamine.

9. The lubricating oil composition according to claim 7 wherein said borated fatty acid ester of glycerol is a mixture containing from 45% to 55% by weight of borated glycerol monooleate and 55% to 45% by weight of borated glycerol dioleate.

10. The lubricating oil composition according to claim 7 wherein the borated fatty acid ester of glycerol is borated glycerol monooleate.

11. A method for reducing the fuel consumption of an internal combustion engine comprising treating the moving surfaces thereof with a composition according to claim 6.

12. A lubricating oil composition according to claim 6 which additionally contains an amount of each of the following:
   (1) from 0.1% to 4% of a Group II metal salt of a dihydrocarbyl dithiophosphoric acid,
   (2) from 0.3% to 10% of a neutral or overbased alkali or alkaline earth metal hydrocarbyl sulfonate or mixtures thereof,
   (3) from 0.2% to 27% of a neutral or overbased alkali or alkaline earth metal, alkylated phenate, or mixtures thereof.

13. The lubricating oil composition according to claim 12 wherein
   (1) said metal salt of the dihydrocarbyl dithiophosphoric acid is zinc dialkyl dithiophosphate wherein the alkyl group contains from 4 to 12 carbon atoms;
   (2) said metal of the neutral or overbased alkali or alkaline earth metal sulfonate is calcium, magnesium or barium or mixtures thereof;
   (3) said metal of the neutral or overbased alkali or alkaline earth metal phenate is calcium, magnesium or barium.

14. The lubricating oil formulation according to claim 12 wherein
   (1) said metal salt of the dihydrocarbyl dithiophosphoric acid is zinc O,O-di(2-ethylhexyl)dithiophosphate, zinc O,O-di(isobutyl/mixed primary hexyl)dithiophosphate, or zinc O,O-di(sec-butyl/mixed secondary hexyl)dithiophosphate;
   (2) said metal salt of the sulfonate is an overbased magnesium or calcium hydrocarbyl sulfonate;
   (3) said metal salt of the phenate is an overbased sulfurized calcium or magnesium monoalkylated phenate.

15. A method for reducing the fuel consumption of an internal combustion engine comprising treating the moving surfaces thereof with a composition according to claim 12.

16. A lubricating oil concentrate comprising 10% to 90% by weight of a lubricating oil and from about 90% to about 10% by weight of a complex prepared by reacting:
   (a) a borated fatty acid ester of glycerol or mixture thereof; and
   (b) an oil soluble alkyl or alkenyl succinimide at 25° C. to 200° C. wherein the wt% ratio of succinimide to borated fatty acid ester of glycerol to form the complex is in the range of 0.5:1 to 3:1.

* * * * *